United States Patent [19]
Washizu et al.

[11] Patent Number: 5,756,134
[45] Date of Patent: May 26, 1998

[54] PROCESS FOR PRODUCING FRUIT FLAVOR

[75] Inventors: Yukio Washizu; Michio Nozaki, both of Kanagawa, Japan

[73] Assignee: Takasago International Corporation, Tokyo, Japan

[21] Appl. No.: 608,604

[22] Filed: Feb. 29, 1996

[30] Foreign Application Priority Data

Mar. 1, 1995 [JP] Japan ................................. 7-065280

[51] Int. Cl.⁶ ............................ A23L 2/02; A23L 2/56
[52] U.S. Cl. ............................ 426/51; 426/533; 426/599
[58] Field of Search ........................... 426/534, 531, 426/532, 533, 599, 616, 615, 51; 435/147

[56] References Cited

U.S. PATENT DOCUMENTS 4,041,185  8/1977  Parliment ........................... 426/534
4,481,292  11/1984 Raymond ........................... 435/147
4,647,466  3/1987  Japikse ........................... 426/387

OTHER PUBLICATIONS

Tani et al. JP61–049577 Abstracted from JPO (=JP362208272).

Primary Examiner—Arthur L. Corbin
Attorney, Agent, or Firm—Sughrue, Mion, Zinn, Macpeak & Seas, PLLC

[57] ABSTRACT

A process for producing a highly fresh and juicy fruit flavor is provided. A recovered aroma derived from a fruit juice, which contains a composition containing (E)-2-hexenol, is contacted with cells of *Candida boidinii* or treated cells of the microorganism to thereby oxidize alcohols and (E)-2-hexenol in the recovered aroma into aldehydes, thus elevating the aldehyde content.

8 Claims, 2 Drawing Sheets

PROCESS FOR PRODUCING FRUIT FLAVOR

FIELD OF THE INVENTION

This invention relates to a process for producing a fruit flavor. More particularly, it relates to a process for producing a highly fresh and juicy fruit flavor by means of microbial oxidation.

BACKGROUND OF THE INVENTION

In recent years, there have been widely employed recovered aromas obtained from fruit juices (i.e., water soluble essences and juice oils) as highly juicy flavors originating in pure fruits ["Koryo no Jiten (Encyclopedia of Flavors)", ed. by M. Fujimaki et al., Asakura Shoten K. K.]. However, these recovered aromas are insufficient in flavor intensity. Thus it has been urgently required to develop fruit flavors having enriched juiciness and freshness and originating in pure fruits.

Due to the needs for the preparation of such flavors and the progress of analytical instruments and separating techniques, the subjects of recent studies on fruit flavor components such as citrus have shifted from peels to fruit juices per se. These studies have clarified key components of juiciness which involve aldehydes such as acetaldehyde and (E)-2-hexenal.

Acetaldehyde is a component which is contained not in citrus peel oil but in the recovered aroma thereof. It is a preferable component capable of imparting a fresh juiciness of citrus flavor. To prepare a citrus flavor with strong and fresh juiciness originating in pure citrus, it is therefore the first requisite how to elevate the acetaldehyde concentration.

On the other hand, (E)-2-hexenal plays an important role in the flavor components of apple and enriches the juiciness of apple. To prepare an apple flavor with strong juiciness originating in pure apple, it is therefore the first requisite how to elevate the (E)-2-hexenal concentration.

The concentrations of acetaldehyde and (E)-2-hexenal in recovered aromas of citrus, apple, etc. may be elevated by concentrating the recovered aromas with the use of an RO membrane or by distillation. However these concentration methods cannot achieve an acetaldehyde or (E)-2-hexenal level exceeding the content thereof inherently contained in the recovered aroma. When the recovered aromas are concentrated 10-fold by distillation, for example, the acetaldehyde concentration is limited to 2 to 3% in the case of citrus or 0.5 to 1.5% in the case of apple and the (E)-2-hexenal concentration is limited to 0.1 to 0.3% in the case of apple.

Accordingly, an object of the present invention is to provide a process for producing a highly fresh and juicy fruit flavor by elevating the aldehyde content in a recovered aroma.

When cultured in a medium containing methanol optionally together with glycerol, *Candida boidinii* AOU-1 and its mutant, *Candida boidinii* SA051, oxidize alcohols into the corresponding aldehydes via a reaction of an enzyme produced by the cells without using any coenzyme [Yoshiaki Tani et al., Agric. Biol. Chem., 49(9), 2699–2706 (1985); and Yasuyoshi Sakai et al., Agric. Biol. Chem., 51(9), 2617–2620 (1987)].

The present inventors have attempted to oxidize alcohols contained in recovered aromas originating in fruits such as citrus or apple into aldehydes including acetaldehyde and (E)-2-hexenal by using cells of *Candida boidinii* or treated cells of the microorganism.

As a result, the present inventors have successfully obtained a highly fresh and juicy fruit flavor by contacting a recovered aroma with cells of *Candida boidinii* or treated cells of the microorganism, which can oxidize alcohols into aldehydes, to thereby elevate the concentrations of aldehydes in the recovered aroma. They have further succeeded in the production of a highly fresh and juicy apple flavor by adding a composition containing (E)-2-hexenol to a recovered apple aroma and then contacting with cells of *Candida boidinii* or treated cells of the microorganism to thereby elevate the concentration of (E)-2-hexenal.

SUMMARY OF THE INVENTION

Accordingly, the present invention provides a process for producing a fruit flavor which comprises contacting a recovered aroma derived from a fruit juice with cells of *Candida boidinii* or treated cells of the microorganism to thereby oxidize alcohols in the recovered aroma into aldehydes. The present invention further provides a process for producing a fruit flavor which comprises adding a composition containing (E)-2-hexenol to the above-mentioned recovered aroma and then contacting the recovered aroma with cells of *Candida boidinii* or treated cells of the microorganism. According to the present invention, alcohols such as ethanol or (E)-2-hexenol, contained in the recovered aroma are converted into aldehydes such as acetaldehyde or (E)-2-hexenal to thereby give a highly fresh and juicy fruit flavor.

DETAILED DESCRIPTION OF THE INVENTION

Figure 1:
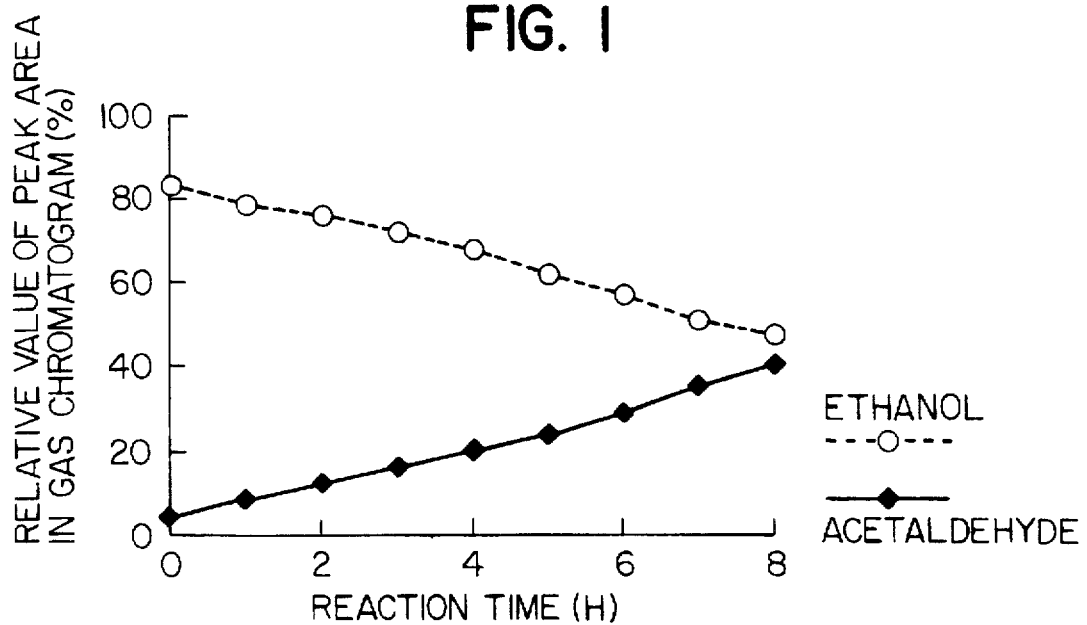
FIG. 1 is a graph which shows changes of the concentrations of ethanol and acetaldehyde contained in the oxidation reaction mixture of Example 1 with the passage of time.

Any recovered aroma derived from a fruit juice can be used as the starting material in the present invention so long as it contains ethanol and/or (E)-2-hexenol. It is particularly preferable to use recovered aromas derived from citrus fruits such as orange or grapefruit and apple.

Such a recovered aroma is a water soluble fraction recovered from the top of the evaporator pipe of the first column of a continuous fruit juice concentrator employed in the industry of manufacturing fruit juices (a temperature accelerated short time evaporator manufactured in United States, a centri-therm evaporator manufactured in Sweden, etc.). In the case of orange, this recovered aroma contains 5 to 10% of ethanol and 0.05 to 0.1% of acetaldehyde, while a recovered apple aroma contains 1 to 2%-of ethanol, 0.01 to 0.03% of (E)-2-hexenol and 0.01 to 0.03% of (E)-2-hexenal. Alternatively, the recovered aromas usable in the present invention are commercially available from, for example, Ernst Gruenewald (Austria), Akras International (Austria), Zick.Zack.Werk (Germany), Indian River Foods (U.S.A.), etc. (All the "%" used herein means "w/v %".)

By adding (E)-2-hexenol or a composition containing the same to the recovered aroma of the present invention, it is possible to obtain an apple flavor which contains (E)-2-hexenal in an elevated amount and has an enriched juiciness. Any composition containing (E)-2-hexenol can be used so long as it contains (E)-2-hexenol together with flavor components originating in natural substances. It is preferable to use a aliphatic $C_6$ alcohol composition containing 25 to 35% of (E)-2-hexenol together with (Z)-3-hexenol, n-hexanol, etc. which is obtained by distilling mint oil originating in Mentha. As an example thereof, the composition employed in Example 2 as will be described hereinafter may be cited. It is preferable to add (E)-2-hexenol in an amount of from 0.003 to 0.3% based on the recovered apple aroma. In the case of a (E)-2-hexenol-containing composition originating in mint, the addition level may be determined so as to control the (E)-2-hexenol content in the composition within the range as defined above.

Any strain can be used in the production process of the present invention so long as it belongs to *Candida boidinii* and is capable of oxidizing alcohols. For example, *Candida boidinii* SA051 strain may be cited. This *Candida boidinii* SA051 strain is a publicly known mutant of *Candida boidinii* and described in Agric. Biol. Chem., 51(8), 2177-2184 (1987). This *Candida boidinii* SA051 strain has been deposited at National Institute of Bioscience and Human-Technology, Agency of Industrial Science and Technology, Japan under the accession number FERM BP-4893 since Nov. 15, 1994 in accordance with the Budapest Treaty.

The *Candida boidinii* SA051 strain which has been cultured in a medium containing methanol alone or a mixture of methanol with glycerol as a carbon source can be used in the process of the present invention. The strain may be pre-cultured. For the preculture, the strain may be cultivated in the presence of not only methanol and glycerol but also other growth promoting substances such as ethanol, glucose, xylose or mannitol. The ability to oxidize alcohols has not been fully elicited from the microbial cells or treated cells thereof which have been cultured in a medium free from methanol, for example, containing glucose alone as a carbon source, and thus alcohols can be hardly oxidized when such cells are used in the present invention.

The media to be used in the cultivation and pre-culture may contain, for example, metabolizable inorganic nitrogen compounds such as ammonium chloride, ammonium sulfate, ammonium phosphate or urea; inorganic salts such as potassium phosphate, potassium dihydrogen phosphate, sodium phosphate, magnesium sulfate, calcium chloride, ferric chloride, ferric sulfate, manganese chloride or manganese sulfate; organic salts such as disodium ethylenediaminetetraacetate; salts of trace elements such as copper, zinc or cobalt; inorganic acids such as boric acid; and vitamins such biotin, thiamine or hydrochloride. Each component can be added in a medium to give a concentration within a range commonly employed in the cultivation of microorganisms. A liquid medium is prepared by dissolving these additives and the above-mentioned carbon source in water. It is not preferable to add organic substances such as yeast extract, meat extract or corn steep liquor to the medium, since they suppress the formation of the alcohol oxidase, which is capable of converting alcohols into aldehydes.

The *Candida boidinii* SA051 strain can be cultured by regulating the medium to about pH 4 to 7 at the initiation of the cultivation and subsequently to pH 4 to 6 under aerobic conditions at a temperature of from 20° to 30° C. for about 50 to 180 hours. It is preferable to cultivate under shaking or stirring with the use of a rotary shaker, a jar fermentor, etc. When a jar fermentor is used, it is recommended to preliminarily add a defoaming agent such as polypropylene glycol to the medium.

During cultivation, methanol (and glycerol) may be repeatedly added as the carbon source to the medium before the methanol (and glycerol) has been completely consumed so as to propagate the microbial cells linearly and elevate the cell density to such a high level as about 100 g (dry basis)/liter. It is preferable to add methanol or a mixture of methanol with glycerol in an amount of about 0.5 to 3% by weight based on the total weight of the medium.

From the thus obtained culture containing the cells of the *Candida boidinii* SA051 strain, the microbial cells are recovered by a separation means such as centrifugation and then suspended in a buffer solution. The resulting suspension is mixed with a recovered aroma derived from a fruit juice, which may contain a composition containing (E)-2-hexenol, and the microbial cells are fully contacted with the recovered aroma originating in fruit by, for example, shaking or stirring to give an oxidation reaction mixture. Instead of the microbial cells per se, the reaction can be carried out using immobilized cells obtained by immobilizing the cultured cells on calcium alginate, carrageenan, liposome and the like carriers, a crude enzyme solution obtained by disrupting the cell membranes of the cultured cells and recovering the solution, an immobilized enzyme obtained by embedding the above-described crude enzyme solution in calcium alginate, carrageenan, liposome and the like or adsorbing it to diatomaceous earth and the like adsorbents. These products are sometimes referred herein to as "treated cells".

It is preferable that the cell concentration in the oxidation reaction mixture ranges from 3 to 60 g (dry cell weight)/l (All the cell weight used herein means dry cell weight). The recovered aromas may be used in an amount of 5 to 20 times as much weight as the weight of the above cell suspension. For example, the amount of the recovered aromas to be added to 100 ml of the cell suspension having a cell density of 3 to 60 g/l ranges from 500 g to 2 kg. The pH value of the oxidation reaction mixture ranges usually from 6 to 10, preferably from 7 to 9. Any buffer solution may be used, so long as the pH value of the oxidation reaction mixture falls within the range as defined above. Although it is possible to simply add an alkali such as sodium hydroxide, it is the most desirable to use a phosphate buffer solution.

The oxidation reaction temperature usually ranges from about 4° to 30° C. The reaction is carried out under aerobic conditions. It may be performed while supplying air or concentrated oxygen gas. The reaction is preferably carried out in a closed system under a pure oxygen atmosphere or while supplying pure oxygen gas under pressure. The reaction time usually ranges from 2 to 8 hours, though it may vary depending on the composition and concentration of the starting alcohols or the like. Thus the reaction time may be determined by measuring the amounts of the produced acetaldehyde and (E)-2-hexenal.

After the completion of the above-mentioned oxidation reaction, the recovered aroma contains 1 to 2% of acetaldehyde in the case of an orange juice or 0.8 to 1.5% of acetaldehyde and 0.03 to 0.1% of (E)-2-hexenal in the case of an apple juice.

The process of the present invention for producing a highly fresh and juicy fruit flavor can be completed by recovering a fraction from the oxidation reaction mixture obtained above preferably by steam distillation.

Namely, after the completion of the reaction, the cells were separated from the oxidation reaction mixture by centrifugation and the like. Then the pH value of the supernatant thus obtained is adjusted to the original pH level of the starting recovered aroma with the use of an inorganic acid such as phosphoric acid or an organic acid such as citric acid. Then, it was subjected to steam distillation under atmospheric or reduced pressure and thus a fraction containing the flavor component is recovered. It is usually appropriate to collect the fraction in an amount of 5 to 30% based on the starting recovered aroma originating in fruit.

The fruit flavor thus obtained contains 6 to 20% of acetaldehyde in the case of orange and 3 to 10% of acetaldehyde and 0.3 to 1.0% of (E)-2-hexenal in the case of apple. Each fruit flavor is highly fresh and juicy.

To further illustrate the present invention in greater detail, and not by way of limitation, the following Examples will be given.

EXAMPLE 1

Cultivation of *Candida boidinii* SA051 strain

Twenty g of glucose, 3 g of ammonium sulfate, 4 g of potassium dihydrogen phosphate, 0.4 g of magnesium sulfate, 10 mg of calcium chloride, 2 mg of manganese chloride, 5 mg of zinc sulfate, 0.05 mg of biotin and 5 mg of thiamine hydrochloride were dissolved in 1,000 ml of deionized water. To the resulting solution was added a 8% by weight aqueous solution of sodium hydroxide to thereby regulate the pH value to 6.0. Thus a liquid medium was prepared. Next, 100 ml of the liquid medium was introduced into a 500-ml ribbed Sakaguchi flask and sterilized in an autoclave at 121° C. for 10 minutes. Then the medium in the flask was inoculated with one loopful of the *Candida boidinii* SA051 strain twice which was then cultured under aeration and shaking with the use of a rotary shaker at 140 rpm at 28° C. for 48 hours to thereby give a pre-culture.

Into a 70-liter jar fermentor were introduced 120 g of glucose, 305.2 g of ammonium chloride, 112.4 g of potassium dihydrogen phosphate, 23.6 g of magnesium sulfate, 2.2 g of calcium chloride, 1.5 g of ferric chloride, 0.68 g of manganese sulfate, 18 g of disodium ethylenediaminetetraacetate, 0.88 g of zinc sulfate, 0.16 g of copper sulfate, 0.11 g of cobalt chloride, 0.1 g of sodium molybdate, 0.16 g of boric acid, 24 mg of potassium iodide, 2 mg of biotin, 200 mg of thiamine hydrochloride and 1.6 g of polypropylene glycol. Then 40 liter of deionized water was added thereto to dissolve these substances. To the solution thus obtained was added a 8% by weight aqueous solution of sodium hydroxide to regulate the pH value to 6.0. Thus a liquid medium was prepared. Next, this liquid medium was sterilized by heating to 121° C. for 10 minutes. Then 800 ml of the above-mentioned pre-culture was added to the medium in the jar fermentor and then cultured under aeration at a rate of 20 liter/min and shaking at 200 rpm at 28° C.

Sixteen hours after the initiation of the cultivation, the pH value was regulated to 5.0 by adding a 8% by weight aqueous solution of sodium hydroxide. Then 400 ml of methanol was added and the cultivation was continued while maintaining the pH value at 5.0. Before the methanol added had been completely consumed, methanol was freshly added in an amount of 1.2% by weight based on the culture and this procedure was repeated. After culturing for 105 hours in total, the cell density in the culture amounted to 48.2 g (dry basis)/liter.

Preparation of concentrated cell suspension

From the culture thus obtained, the cells were separated by centrifugation and washed with a 0.1M phosphate buffer solution (pH 7.5). Then the cells were suspended again in a 0.1M phosphate buffer solution to give a cell density of 148.5 g (dry basis)/liter. Thus a concentrated cell suspension was obtained.

Figure 2:
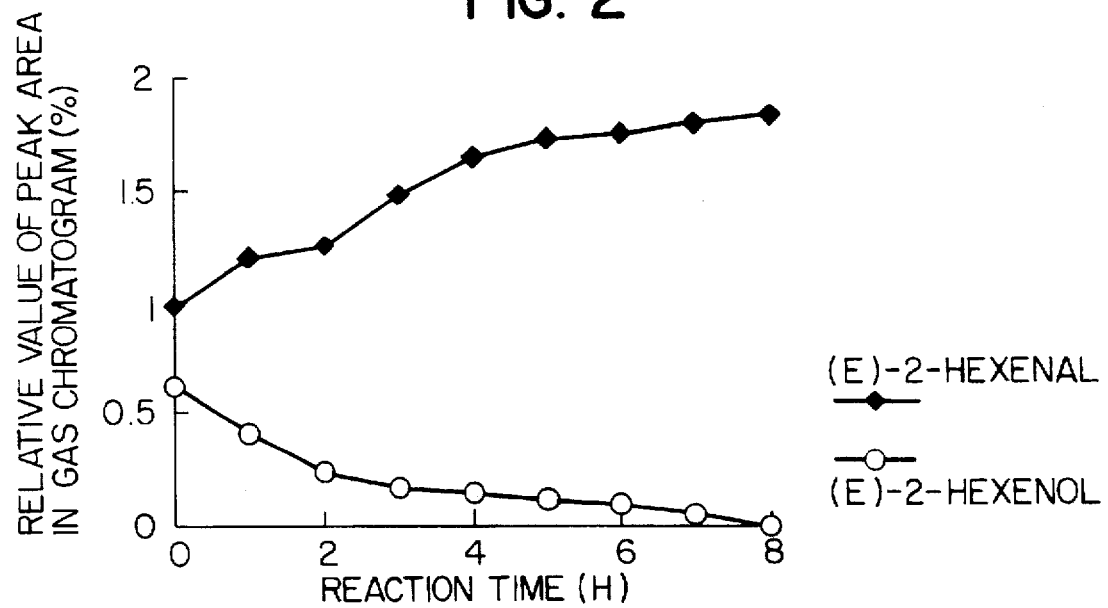
FIG. 2 is a graph which shows changes of the concentrations of (E)-2-hexenol and (E)-2-hexenal contained in the oxidation reaction mixture of Example 1 with the passage of time.

Production of fruit flavor 2 kg of a recovered apple aroma (manufactured by Ernst Grunewald; containing 1.8% of ethanol, 0.07% of acetaldehyde, 0.02% of (E)-2-hexenol and 0.03% of (E)-2-hexenal), 46 ml of the concentrated cell suspension as obtained above and 140 ml of a 1M phosphate buffer solution (pH 7.5) were introduced into a 5-liter jar fermentor. Then the mixture was stirred at 350 rpm at 15° C. for 8 hours while supplying pure oxygen gas at a rate of 200 ml/min to thereby give an oxidation reaction mixture. FIGS. 1 and 2 show changes of the ethanol and acetaldehyde concentrations and (E)-2-hexenol and (E)-2-hexenal concentrations in the reaction mixture with the passage of time. The oxidation reaction mixture thus obtained was centrifuged (4,000 rpm, 20 minutes) to thereby eliminate the cells and then regulated to pH 5.4 by adding phosphoric acid. This solution was subjected to steam distillation under atmospheric pressure to recover 100 g of a fraction. Then 100 g of 95% ethanol was added to this fraction to give an apple flavor A. This apple flavor A contained 7% of acetaldehyde and 0.5% of (E)-2-hexenal.

EXAMPLE 2

Preparation of composition containing (E)-2-hexenol

A marketed spearmint oil (manufactured by A M TODD) was distilled and the first fraction [distillation temperature: 70°–80° C. (13–18 mmHg), ratio to spearmint oil: 10%] was collected. Next, this fraction was subjected to precision distillation again [distillation temperature: 70°–80° C. (13–18 mmHg)] to eliminate azeotropic impurities due to the first distillation. Then it was subjected to column chromatography [stationary phase: silica gel 60 (manufactured by Merck), mobile phase: n-hexane:ethyl acetate=–98:2] and the thus eluted matters were eliminated. Subsequently, a mixture of n-hexane with ethyl acetate (80:20) was passed through the stationary phase and the eluate was collected. After eliminating n-hexane and ethyl acetate in the collected eluate, a purified (E)-2-hexenol-containing composition was obtained (yield based on spearmint oil: 0.08%). This (E)-2-hexenol-containing composition contained 32.6% by weight of (E)-2-hexenol, 45.3% by weight of (Z)-3-hexenol, 16.2% by weight of n-hexanol and other aliphatic $C_6$ alcohol isomers.

Production of fruit flavor

Figure 3:
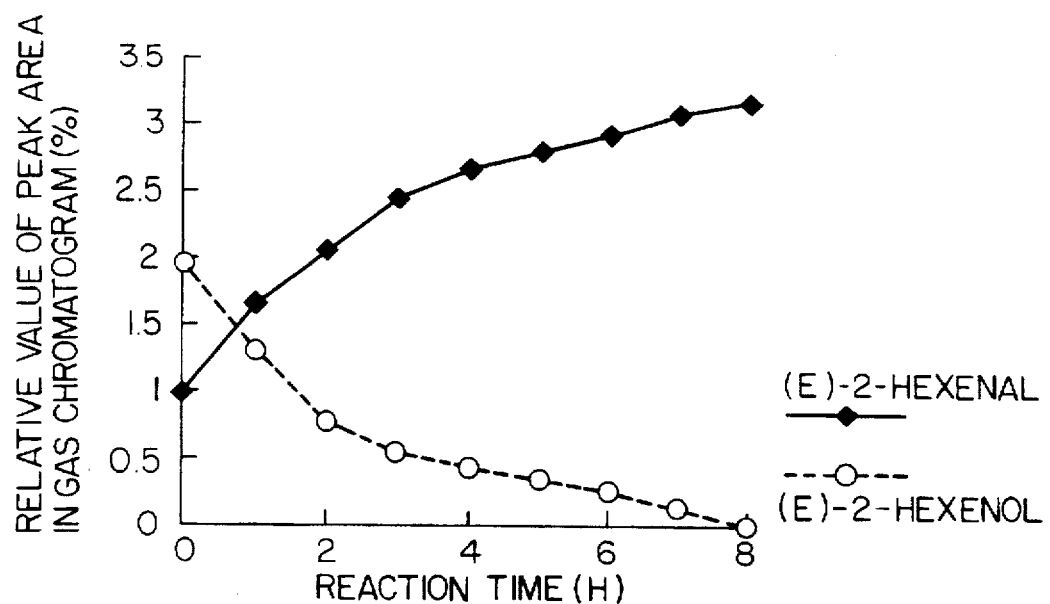
FIG. 3 is a graph which shows changes of the concentrations of (E)-2-hexenol and (E)-2-hexenal contained in the oxidation reaction mixture of Example 2 with the passage of time.

The procedure of Example 1 was repeated by using the recovered apple aroma, the concentrated cell suspension and the phosphate buffer solution, each the same as employed in Example 1, and additionally using 2 g of the composition containing (E)-2-hexenol as obtained above to give an oxidation reaction mixture. FIG. 3 shows changes of the (E)-2-hexenol and (E)-2-hexenal concentrations in this oxidation reaction mixture with the passage of time. The oxidation reaction mixture thus obtained was treated in the same manner as described in Example 1 to give an apple flavor B. This apple flavor B contained 7% of acetaldehyde and 0.8% of (E)-2-hexenal.

EXAMPLE 3

Figure 4:
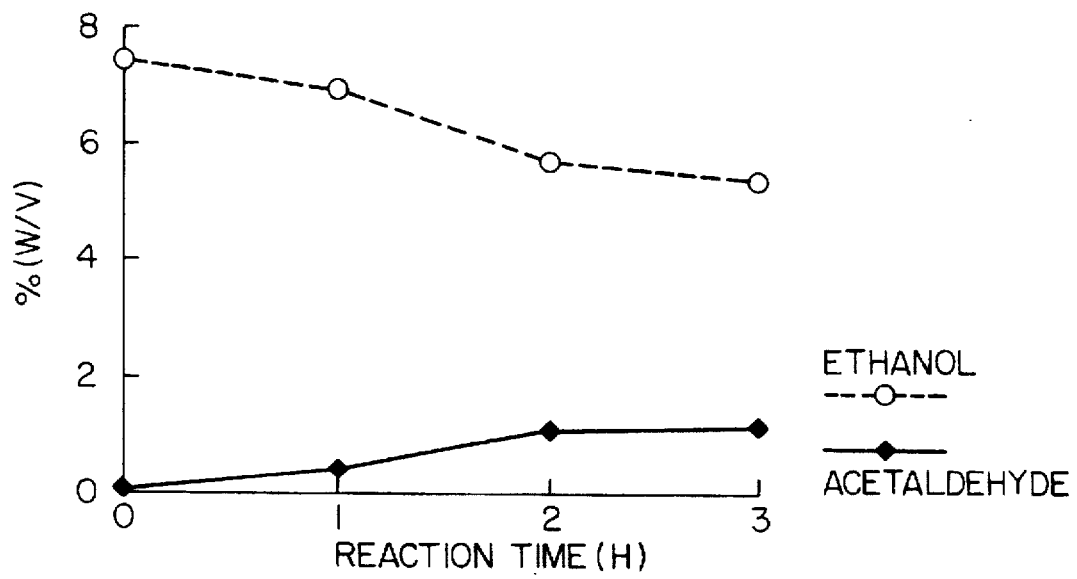
FIG. 4 is a graph which shows changes of the concentrations of ethanol and acetaldehyde contained in the oxidation reaction mixture of Example 3 with the passage of time.

The procedure of Example 1 was repeated using 2 kg of a recovered orange aroma (manufactured by-Indian River Foods, containing 7.4% of ethanol and 0.07% of acetaldehyde) in place of the recovered apple aroma and stirring for 3 hours to give an oxidation reaction mixture. FIG. 4 shows changes of the ethanol and acetaldehyde concentrations in this reaction mixture with the passage of time. The reaction mixture thus obtained was regulated to pH 4.0 with phosphoric acid and cells were eliminated therefrom by centrifugation. Then the supernatant was subjected to steam distillation under atmospheric pressure to thereby give 320 g of a fraction which was referred to as an orange flavor A. This orange flavor A contained 18% of acetaldehyde.

EXAMPLE 4

The procedure of Example 3 was repeated except for performing the steam distillation under reduced pressure (40°–41° C., 50–60 mmHg). Thus 320 g of a fraction was obtained and referred to as an orange flavor B. This orange flavor B contained 5% of acetaldehyde.

TEST EXAMPLE

Sensory evaluation test

An apple flavor C, an orange flavor C and an orange flavor D were produced as control flavors by conducting distillation in the same manner as in Example 1, Example 3 (under atmospheric pressure) and Example 4 (under reduced pressure), respectively, each without microbial oxidation reaction. These controls and the apple flavors A and B and the orange flavors A and B obtained in Examples 1 to 4 were added to a fruit juice-free drink (formulation 1) and fruit juice drinks (formulation 2) and sensorially evaluated by 10 skilled panelists of the applicant's institute.

Formulation 1

Five g of each flavor was added to a drink having the following composition.

| granulated sugar | 100 g |
| citric acid | 0.1 g |
| deionized water | q.s. to 1,000 ml. |

Formulation 2

Two g of each orange flavor was added to a drink having the following composition.

| orange juice (concentrated 6-fold) | 100 g |
| deionized water | q.s. to 600 ml. |

1.7 g of each apple flavor was added to a drink having the following composition.

| apple juice (concentrated 5-fold) | 100 g |
| deionized water | q.s. to 500 ml. |

Results of sensory test

Table 1 shows the average scores evaluated in 5 grades (5: very good, 4: good, 3: moderate, 2: poor, 1: very poor). The apple flavors and the orange flavors obtained by the production process of the present invention were excellent in having strong freshness and juiciness.

TABLE 1

| | Fruit juice-free drink | Fruit juice drink | Evaluation (Remarks) |
|---|---|---|---|
| Apple flavor A | 4.6 | 4.5 | highly fresh |
| Apple flavor B | 4.8 | 4.7 | highly fresh and juicy |
| Apple flavor C | 2.9 | 2.8 | |
| Orange flavor A | 4.3 | 4.4 | highly fresh and juicy |
| Orange flavor C | 3.1 | 3.0 | |
| Orange flavor B | 4.4 | 4.4 | highly fresh |
| Orange flavor D | 2.9 | 2.7 | |

According to the present invention, the contents of aldehydes such as acetaldehyde or (E)-2-hexenal in a recovered aroma can be elevated to give a highly fresh and juicy fruit flavor.

While the invention has been described in detail and with reference to specific examples thereof, it will be apparent to one skilled in the art that various changes and modifications can be made therein without departing from the spirit and scope thereof.

What is claimed is:

1. A process for producing a fruit flavor which comprises contacting a recovered aroma, derived from a fruit juice and containing alcohols comprising (E)-2-hexenol, with cells of *Candida boidinii* or treated cells of *Candida boidinii* to oxidize alcohols containing (E)-2-hexenol in the recovered aroma into aldehydes containing (E)-2-hexenal.

2. A process for producing a fruit flavor as claimed in claim 1, wherein said recovered aroma contains (E)-2-hexenol in an amount of from 0.01 to 0.03%.

3. A process for producing a fruit flavor as claimed in claim 1, wherein said fruit flavor contains (E)-2-hexenal which is formed by oxidization of the (E)-2-hexenol.

4. A process for producing a fruit flavor as claimed in claim 1, wherein said recovered aroma is a recovered aroma derived from an apple juice.

5. A process for producing a fruit flavor as claimed in claim 4, wherein (E)-2-hexenol or a composition containing (E)-2-hexenol is added to the recovered aroma prior to contacting said aroma with cells of *Candida boidinii*.

6. A process for producing a fruit flavor as claimed in claim 1, wherein (E)-2-hexenol or a composition containing (E)-2-hexenol is added to the recovered aroma prior to contacting said aroma with cells of *Candida boidinii*.

7. A process for producing a fruit flavor which comprises contacting a recovered aroma, derived from a fruit juice and containing alcohols comprising (E)-2-hexenol, with cells of *Candida boidinii* or treated cells of *Candida boidinii* under atmospheric pressure or reduced pressure to oxidize alcohols containing (E)-2-hexenol in the recovered aroma into aldehydes containing (E)-2-hexenal.

8. The process for producing a fruit flavor as in claim 7, wherein said cells of *Candida boidinii* or treated cells of *Candida boidinii* are cells of *Candida boidinii* SA051 strain.

* * * * *